US 8,676,230 B2

(12) United States Patent
Alexander et al.

(10) Patent No.: US 8,676,230 B2
(45) Date of Patent: Mar. 18, 2014

(54) BIO SIGNAL BASED MOBILE DEVICE APPLICATIONS

(75) Inventors: Zavier Alexander, San Jose, CA (US);
Cheng-I Chuang, San Jose, CA (US);
Johnny Liu, San Jose, CA (US); David Westendorf, San Jose, CA (US);
KooHyoung Lee, San Jose, CA (US)

(73) Assignee: NeuroSky, Inc., San Jose, CA (US)

( * ) Notice: Subject to any disclaimer, the term of this patent is extended or adjusted under 35 U.S.C. 154(b) by 37 days.

(21) Appl. No.: 13/466,852

(22) Filed: May 8, 2012

(65) Prior Publication Data

US 2012/0295589 A1 Nov. 22, 2012

Related U.S. Application Data

(60) Provisional application No. 61/486,649, filed on May 16, 2011.

(51) Int. Cl.
*H04W 24/00* (2009.01)
(52) U.S. Cl.
USPC .................................... 455/456.1; 455/556.1
(58) Field of Classification Search
USPC ........ 455/410–411, 456.1–457, 414.1–414.4, 455/550.1, 556.1, 575.2, 575.6; 382/115; 482/8–9
See application file for complete search history.

(56) References Cited

U.S. PATENT DOCUMENTS

| | | | |
|---|---|---|---|
| 6,605,038 B1 * | 8/2003 | Teller et al. .................... 600/300 |
| 2002/0082007 A1 * | 6/2002 | Hoisko et al. .................. 455/426 |
| 2004/0209600 A1 * | 10/2004 | Werner et al. ............... 455/414.1 |
| 2005/0052348 A1 | 3/2005 | Yamazaki et al. |
| 2005/0085257 A1 * | 4/2005 | Laird et al. .................. 455/550.1 |
| 2005/0124463 A1 | 6/2005 | Yeo et al. |
| 2005/0208969 A1 * | 9/2005 | Kwoen ......................... 455/557 |
| 2007/0287596 A1 * | 12/2007 | Case et al. ........................ 482/8 |
| 2008/0177197 A1 | 7/2008 | Lee et al. |
| 2008/0208016 A1 | 8/2008 | Hughes et al. |
| 2009/0023428 A1 * | 1/2009 | Behzad et al. ............. 455/414.3 |
| 2010/0081895 A1 | 4/2010 | Zand |
| 2010/0286533 A1 | 11/2010 | Lee et al. |
| 2010/0331649 A1 | 12/2010 | Chou |

* cited by examiner

*Primary Examiner* — George Eng
*Assistant Examiner* — Marcus Hammonds
(74) *Attorney, Agent, or Firm* — Van Pelt, Yi & James LLP

(57) ABSTRACT

Techniques for providing bio signal based mobile device applications are disclosed. In some embodiments, a system for bio signal based mobile device applications includes a bio signal sensor (e.g., biosensor) or multiple biosensors (e.g., multiple biosensors for EEG detection, or multiple biosensors that can each detect different types of bio signals), a bio signal processing unit, the mobile device, and a software application(s) that utilize the bio signal information for various applications (e.g., practical applications, entertainment applications, social networking applications, and/or other applications).

15 Claims, 7 Drawing Sheets

BIO SIGNAL BASED MOBILE DEVICE APPLICATIONS

CROSS REFERENCE TO OTHER APPLICATIONS

This application claims priority to U.S. Provisional Patent Application No. 61/486,649 entitled BIO SIGNAL BASED MOBILE DEVICE APPLICATIONS filed May 16, 2011 which is incorporated herein by reference for all purposes.

BACKGROUND OF THE INVENTION

The number of smart phone and other mobile device users worldwide is estimated to exceed 1 billion by 2013. Smart phone and mobile devices are increasingly equipped with multiple sensors, such as sensors that can capture sound, photographs, video, acceleration/velocity, orientation, and location/GPS. The increasing processing power and sensor functionality of such devices provides for a rich platform for applications that can utilize this information for various purposes. For example, applications exist that utilize such audio, video, and/or location functionality for practical/productive applications and entertainment applications.

BRIEF DESCRIPTION OF THE DRAWINGS

Various embodiments of the invention are disclosed in the following detailed description and the accompanying drawings.

DETAILED DESCRIPTION

Figure 1:
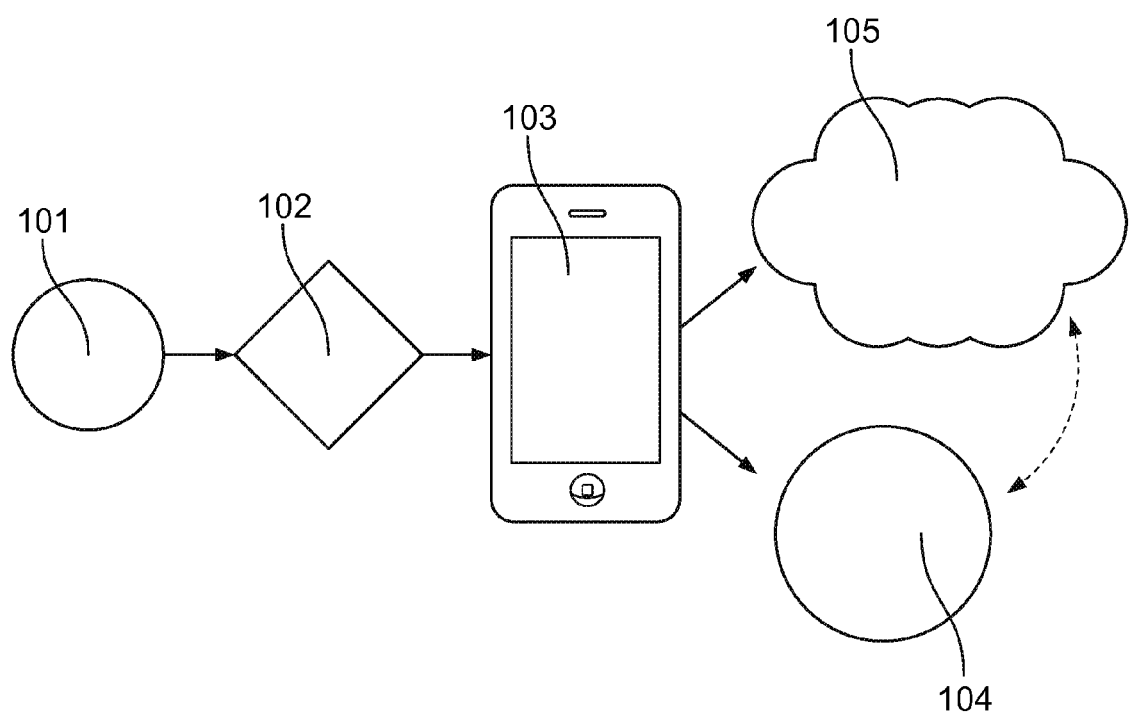
FIG. 1 illustrates a functional diagram of acquisition and use of bio signal data by a device or applications executed on the device in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Smart phone and mobile devices are increasingly equipped with multiple sensors, such as sensors that can capture sound, photographs, video, acceleration/velocity, orientation, and location/GPS. The increasing processing power and sensor functionality of such devices provides for a rich platform for applications that can utilize this information for various purposes. For example, applications exist that utilize such audio, video, and/or location functionality for practical/productive applications and entertainment applications.

Although various smart phone and mobile devices are adept at detecting information regarding their own state and the world around them (e.g., location, network connectivity/availability state, proximity to other devices, and/or various other information), their ability to detect and respond to the physical, physiological and/or psychological state of a human user is limited or nonexistent. Mobile devices generally lack any type of biosensor that can be used to inform and modify device behavior, act as a control mechanism, or can provide data for use in applications. Smart phones and other advanced mobile electronics have improved greatly in their ability to sense their position in space and the environment around them, yet still have no insight into the physical, physiological, and/or psychological state of their user. This is an obstacle to the development of advanced user-aware interfaces and applications.

What are needed are techniques for such devices to detect and respond to various physical, physiological, and psychological states of a human user. Accordingly, techniques for providing various bio signal based mobile device applications are disclosed. In some embodiments, mobile devices include smart phones and other types of cellular phones/devices, tablet computers, laptop computers, GPS devices, portable digital music/video devices, portable gaming devices, and other types of mobile/portable computing devices, generally referred to herein as mobile devices. In some embodiments, mobile devices include various sensors/sensor functionality that can detect a user's bio signals, such as ElectroCardioGraphy (ECG), ElectroEncephalography (EEG), ElectroMyoGraphy (EMG), ElectrOculoGraphy (EOG), Galvanic Skin Response (GSR), Body Temperature, Heart/Pulse Rate, and other bio signals.

Various new and innovative applications can be provided that use enhanced interfaces for mobile devices based on various bio signals detection and monitoring. For example, by integrating biosensors into the feature rich environment of the mobile device, the addition of the user's physiological data gathered by the biosensor, in combination with the audio, multi-media, location, and/or movement data already collected by the mobile device provides a new platform for advanced user-aware interfaces and innovative applications.

In some embodiments, a mobile device includes various biosensors (e.g., bio signal sensors) capable of detecting bio signals, such as bio signal sensors for detection/monitoring of one or more of the following: ECG, EEG, EMG, EOG, GSR, body temperature, and heart/pulse rate. For example, the user can either actively choose to interact with the bio signal sensors for a specific function or have the sensors passively detect/monitor certain bio signal information. This information can be stored on the device itself, shared with other devices through a direct connection, or communicated to remote devices or services/applications over a network communication. Applications can then use this information for performing certain functions.

In some embodiments, a system for bio signal based mobile device applications includes a bio signal sensor (e.g., biosensor) or multiple biosensors (e.g., multiple biosensors for EEG detection, or multiple biosensors that can each detect different types of bio signals), a bio signal processing unit, the mobile device, and a software application(s) that utilize the bio signal information for various applications (e.g., practical applications, entertainment applications, social networking applications, and/or other applications). The biosensors and the bio signal unit can be integrated into the structure of the mobile device, although other configurations are also possible. In some embodiments, the bio signal unit is implemented in an integrated circuit configured or designed for a particular use, such as in an Application-Specific Integrated Circuit (ASIC) or Field-Programmable Gate Array (FPGA). In some embodiments, the bio signal unit is implemented as a software engine executed on a general processor of the mobile device.

For example, the user can activate the biosensors in a specific configuration to begin collecting information. How and if the user activates the biosensors can depend on the specific sensor configuration and what data is being collected. For example, a user collecting ECG and heart rate data may need to touch several dry sensors with both hands or capacitive (e.g., non-contact) sensors can be used which allow ECG and heart rate data to be collected by simply placing the sensor close to the chest, or an oxymetric sensor can be used to measure the heart rate at finger tip. How the collected information is used, how the user interacts with it, and the content of the experience is generally dependent on the nature of the application the user executes on the mobile device.

FIG. 1 illustrates a functional diagram of acquisition and use of bio signal data by a device or applications executed on the device in accordance with some embodiments. As shown, a biosensor 101 detects a bio signal, collects the detected bio signal data, and sends the detected bio signal data to a bio signal processing unit 102, which is in communication with a mobile device 103. For example, the biosensor 101 and bio signal processing unit 102 can be integrated within the mobile device 103 or can be provided as a wired or wireless attached accessory, such as the mobile device's protective case, wireless headset, or various other form factors. As also shown, the mobile device 103 communicates the bio signal data to an application 104. For example, the application can utilize the bio signal data for a desired feature in real time or store information locally and/or communicate the information with an online server or other remote storage device 105, which applications can draw data from, such as for a cloud based application or cloud service. The stored data can include an individual user's bio signal information or aggregated bio signal information of several different users. Applications can form their own archives of data for use with their own user base or all bio signal data can be archived at a central data storage location/service. For example, the application can be a software application that executes locally on a general processor of the mobile device, or software/firmware running on a separate device, or a web based service (e.g., which can use locally processed information, such as based on the bio signal detection and interpretation, with remote/web based application/service functionality, such as a social networking service and/or any other remote/web based application/service functionality).

Figure 2:
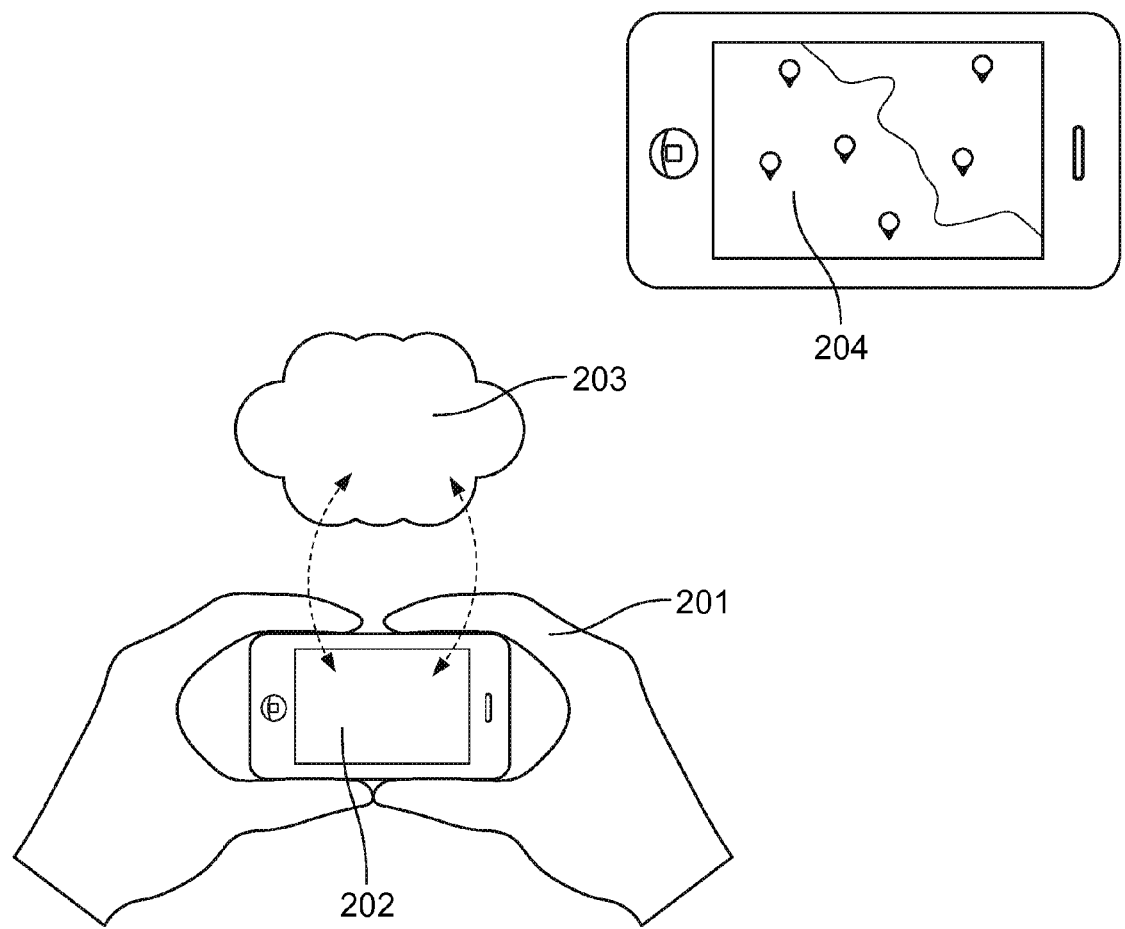
FIG. 2 illustrates a dynamic map application that uses bio signal data to show social "hot spots" in a geographic area in accordance with some embodiments.

FIG. 2 illustrates a dynamic map application that uses bio signal data to show social "hot spots" in a geographic area in accordance with some embodiments. Specifically, FIG. 2 illustrates a dynamic map application that uses bio signal data (e.g., ECG, EEG, EMG, EOG, GSR, body temperature, and/or heart/pulse rate data) in concert with GPS coordinates to provide a physiological context to geography. For example, the user, through the user's hands 201, can interact with biosensors on a mobile device 202, which can collect various bio signals sensed through various biosensors, such as pulse and heart rate information. The user's detected bio signal data is then sent to a map application's central archive 203 where bio signal data from one or more users is aggregated and organized by location. For example, this collected and aggregated bio signal information of various users can then be graphically overlaid in a display with a map of the user's selected location 204. Various applications can be provided using the combination of location information and various bio signal sensor detected information.

For example, a dynamic map application can display specific location points on the map where detected user heart rates are generally high to generally low, which can provide a subjective context for the level of excitement in each area or social "hot spots" by geographic area based on detected heart rates.

As another example, a dynamic map application can be provided that uses ECG data in concert with GPS coordinates and/or various other sensor captured data (e.g., picture, video, and/or audio data) to provide physiological context to the user's geographical surroundings. The user can interact with several ECG sensors on the mobile device 202 with both hands 201 to begin collecting bio signal, such as pulse and heart rate, information. Their ECG data can then be sent to the dynamic map application's central archive 203 where ECG data from one or more users is aggregated and organized by location. This information can be graphically overlaid in a display with a map of the user's selected location 204 to display specific points where user heart rates are generally high to generally low, which can provide a subjective context for the level of excitement in each area.

As yet another example, a dynamic map application can be provided that uses EMG data in concert with GPS coordinates and/or various other sensor captured data (e.g., picture, video, and/or audio data) to provide physiological context to the user's geographical surroundings. The user can interact with several EMG sensors on the mobile device 202 with both hands 201 to begin collecting bio signal data, such as muscle movement information. Their EMG data can then be sent to the dynamic map application's central archive 203 where EMG data from one or more users is aggregated and organized by location. This information can be graphically overlaid in a display with a map of the user's selected location 204 to display specific points where user movement is generally high to generally low, which can provide a subjective context for the level of physical activity in each area.

As yet another example, a dynamic map application can be provided that uses EEG data in concert with GPS coordinates and/or various other sensor captured data (e.g., picture, video, and/or audio) to provide physiological context to the user's geographical surroundings. The user can hold the mobile device 202 in contact with the user's head to allow for the embedded EEG sensor(s) to be in contact with the user's head or the user can wear a headset with several EEG sensors, which can be in communication with the mobile device 202 and in contact, for example, with the user's head, to begin collecting EEG signal data. Their EEG data can then be sent to the dynamic map application's central archive 203 where EEG data from one or more users is aggregated and organized by location. The EEG data can be processed to evaluate the user's attention or other mental states (e.g., relaxation, anxiety, drowsiness, and/or sleep) using various techniques, such as described in U.S. patent application Publication No. 2008/0177197, entitled "Method and Apparatus for Quantitatively Evaluating Mental States Based on Brain Wave Signal Processing System" assigned to NeuroSky, Inc. This information can be graphically overlaid in a display with a map of the user's selected location 204 to display specific points where user attention is generally high to generally low, which can provide a subjective context for the level of interest in each area.

As yet another example, various combinations of biosensors can be provided in concert with GPS coordinates and/or various other sensor captured data (e.g., picture, video, and/or audio) to provide physiological context to the user's geographical surrounding to provide various functions and features as similarly discussed above and/or new functions or features using the various combinations of bio signal input from various biosensors.

Figure 3:
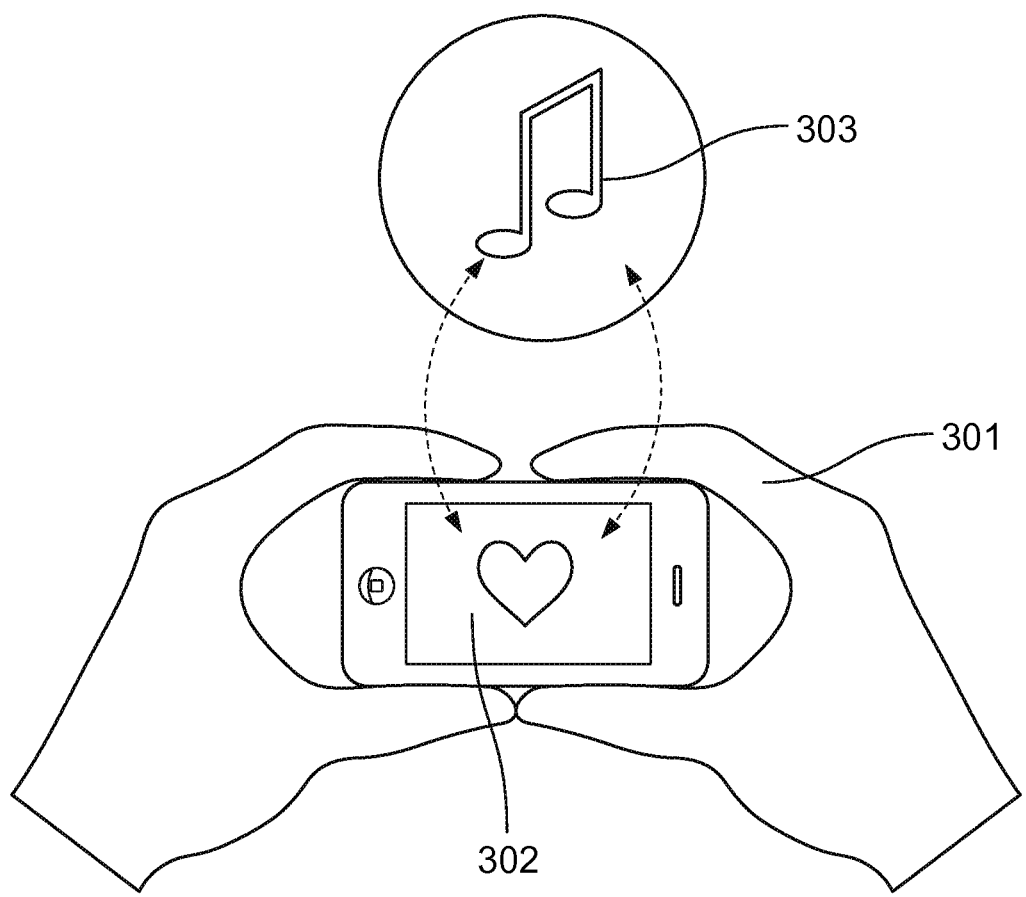
FIG. 3 illustrates a dynamic music application that senses a user's pulse to trigger context sensitive music in accordance with some embodiments.

FIG. 3 illustrates a dynamic music application that senses a user's pulse to trigger context sensitive music in accordance with some embodiments. Specifically, FIG. 3 illustrates a dynamic music application 303 that is responsive to the user's heart rate sensed through the user's hands 301 holding a mobile music device 302 during, for example, physical activity for the purpose of driving the user towards a subjective or objective optimal heart rate dependant on the activity (e.g., cycling, running, or another activity or exercise). For example, songs can be preselected by users to either excite them during the activity or relax them to cool down, or determined from an online database of songs suggested based on other user data. When the user interacts with the biosensors, the music application 303 uses the processed bio signal data and selects the next song(s) to play based on user configured settings and the detected bio signal data, such as meeting a specific heart rate target range, a length of time in the activity, genres of music, and/or other qualities or criteria.

Figure 4:
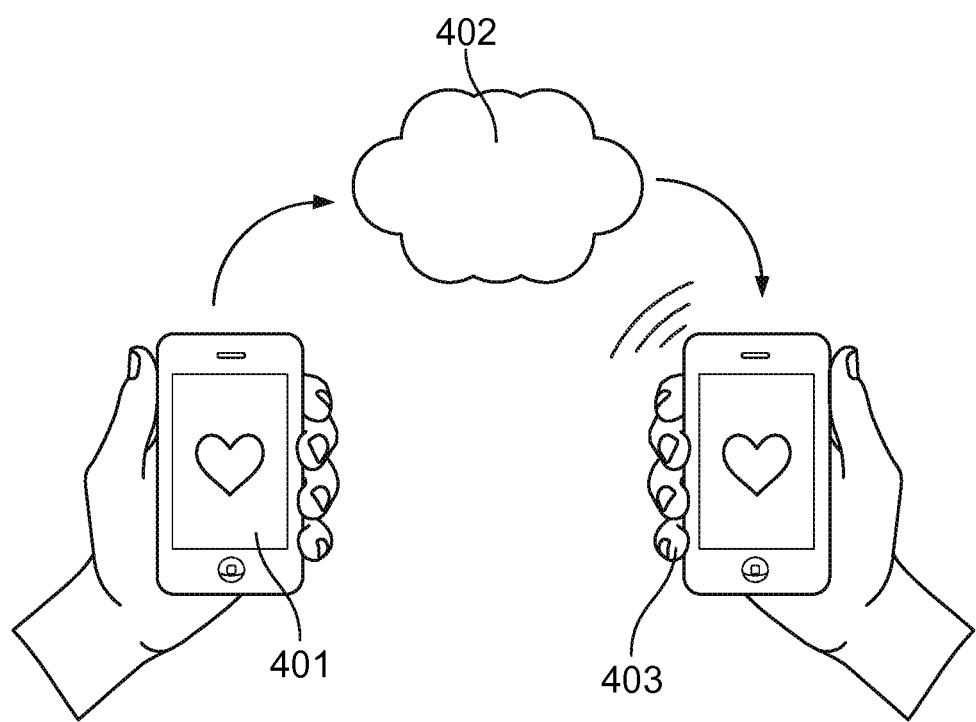
FIG. 4 illustrates a dynamic social application that allows the receiver of a mobile device communication to use a user's pulse as their ring tone (e.g., or other hailing signal) in accordance with some embodiments.

FIG. 4 illustrates a dynamic social application that allows the receiver of a mobile device communication to use a user's pulse as their ring tone (e.g., or other hailing signal) in accordance with some embodiments. Specifically, FIG. 4 illustrates a dynamic social application that acquires a user's heart rate, and/or other bio signal(s), before placing a call, texting, or engaging in other forms of mobile device to mobile device communication and modifies the ring tone (e.g., or other hailing signal) of the receiving mobile device based on the caller's pulse or other bio signal. For example, the caller can interact with biosensors on the mobile device to record their pulse. This data can be saved locally on the mobile device for later use when a call is placed, if desired. The user can then place a call from a mobile device 401, and their pulse information can be sent to an application server 402. If the receiver of the call has a dynamic social application that can process the pulse information, then the pulse information can be sent to their mobile device 403 from the application server 402 and can modify their default ring tone (e.g., or other hailing signal) based on the pulse to play a sound of the caller's pulse, or engage another desired effect as shown at the called user's mobile device 403. The receiver of the call can also choose to send back his or her own pulse data to the caller.

In some embodiments, a dynamic social application includes executing a dynamic social application using a processed bio signal, in which the dynamic social application includes sharing the processed bio signal associated with a first user with a second user (e.g., the second user has a social relationship with the first user, such as a friend relationship, family relationship, co-worker relationship, and/or a medical or doctor-patient relationship). In some embodiments, the processed bio signal is shared with a group of users associated with the first user (e.g., friends, family, co-workers, and/or a group of medical professionals). In some embodiments, the processed bio signal is shared with an entity, such as a database, an application, or another device (e.g., which can be accessed by one or more other users, which are associated with the first user). In some embodiments, others can monitor the bio signal in real-time or pseudo real-time through mobile devices via communication networks (e.g., the Internet, cellular, and other wired and/or wireless networks). For example, the various techniques described herein can be used to check a user's physical, physiological, and/or psychological (e.g., cognitive and emotional) states (e.g., if bio signals exceed certain thresholds or normal ranges, then a warning can be provided to the user or to a designated third party, such as a family contact, friend, and/or medical contact, such as a doctor).

In some embodiments, a bio signal is used to identify a person. For example, a processed bio signal can be used to individualize a user associated with a mobile device as a biometric related security check for use of the mobile device (e.g., ECG and/or EEG signals can be used as another security measure, similar to a password or fingerprint, to verify that the user is authorized to use the mobile device, such as an owner of the mobile device).

Figure 5:
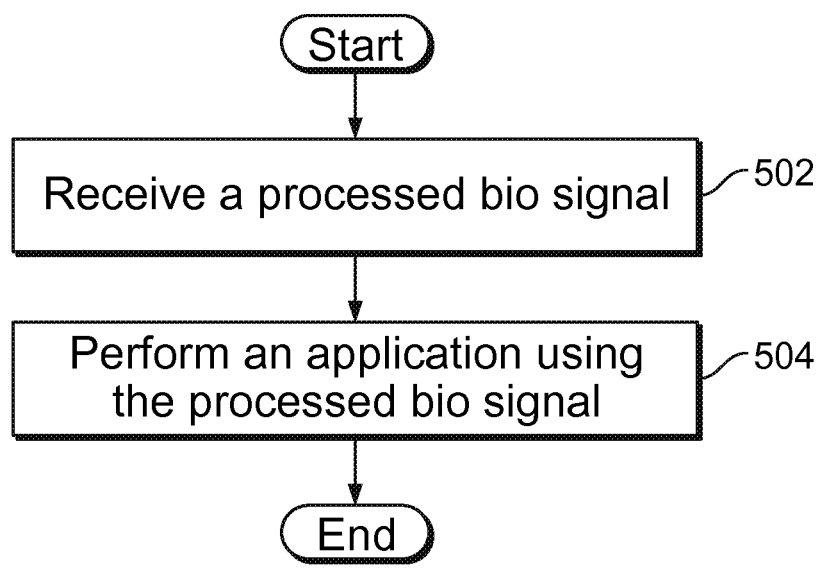
FIG. 5 illustrates a flow diagram for an application using bio signal data in accordance with some embodiments.

FIG. 5 illustrates a flow diagram for an application using bio signal data in accordance with some embodiments. At 502, a processed bio signal is received. At 504, an application using the processed bio signal is performed.

Figure 6:
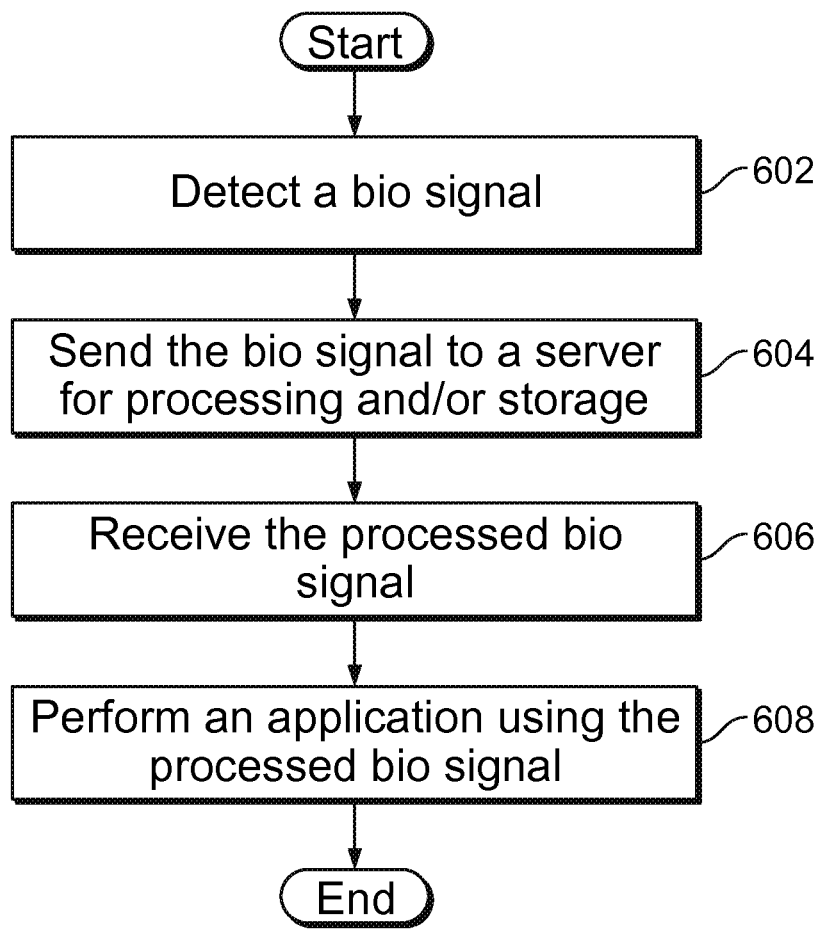
FIG. 6 illustrates another flow diagram for an application using bio signal data in accordance with some embodiments.

FIG. 6 illustrates another flow diagram for an application using bio signal data in accordance with some embodiments. At 602, a bio signal is detected (e.g., using a bio sensor). At 604, the bio signal is sent to a server for processing and/or storage. At 606, the processed bio signal is received. At 608, an application is performed using the processed bio signal.

Figure 7:
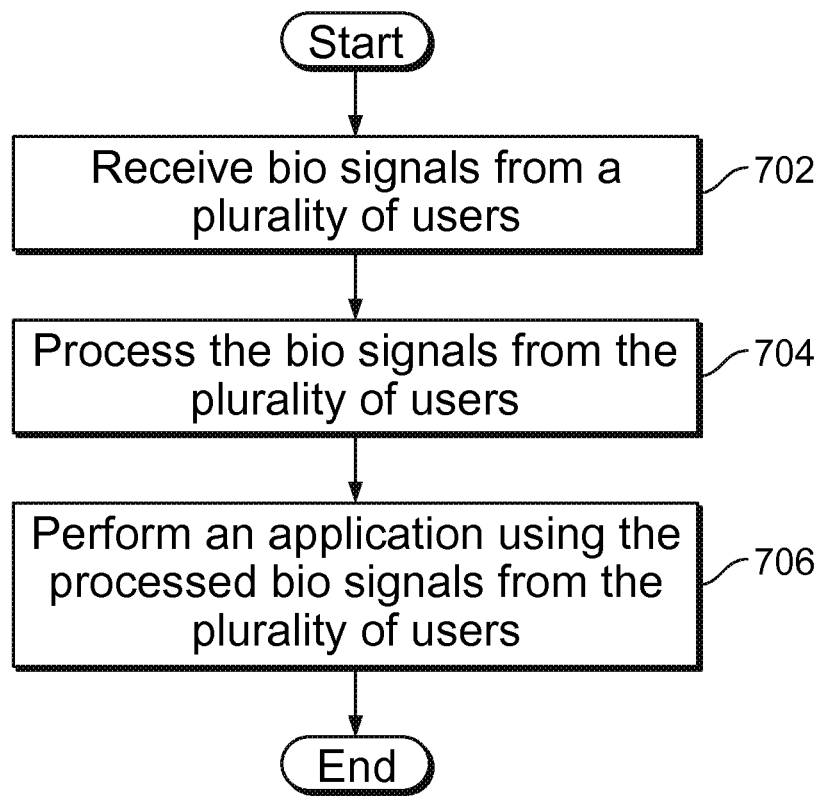
FIG. 7 illustrates a flow diagram for an application using bio signal data from a plurality of users in accordance with some embodiments.

FIG. 7 illustrates a flow diagram for an application using bio signal data from a plurality of users in accordance with some embodiments. At 702, bio signals from a plurality of users are received. At 704, the bio signals from the plurality of users are processed. At 706, an application using the processed bio signals from the plurality of users is performed.

As will now be apparent, various other bio signal based mobile device applications can be provided using the various techniques described herein. For example, different types of mobile devices, different combinations of bio signal sensors, and different types of applications and/or services that can use various forms of bio signal data as input, can be provided to facilitate a vast array of new applications, such as for productivity, entertainment, social networking, advertisement placement and targeting, and/or various other types of applications.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for bio signal based mobile device applications, comprising:
a processor configured to:
receive a processed bio signal of a user, the bio signal being an ElectroCardioGraphy (ECG) signal, an ElectroEncephalography (EEG) signal, an ElectroMyoGraphy (EMG) signal, an ElectrOculoGraphy (EOG) signal, an Galvanic Skin Response (GSR) signal, or any combination thereof;
determine whether the user is an authorized user of a mobile device, wherein the determining comprises:
compare the received bio signal with a stored bio signal of the authorized user of the mobile device; and
in the event that the user is an authorized user of the mobile device, execute a dynamic map application using the processed bio signal, wherein the executing of the dynamic map application comprises:
receive collected and aggregated processed bio signals of other users;
measure a level of the processed bio signals of the other users and a level of the received processed bio signal of the user based on a location;
overlay the level of the measured processed bio signals of the other users and the level of the measured processed bio signal of the user on a map corresponding to the location;
combine the level of the measured processed bio signals in concert with the location with data acquired via another sensor relating to the location, the data including picture, video, audio data, or any combination thereof; and
display the level of the processed bio signals of the other users with the level of the received processed bio signal of the user on the map; and
a memory coupled to the processor and configured to provide the processor with instructions.

2. The system recited in claim 1, wherein the processor is further configured to:
send the bio signal to a server for storage.

3. The system recited in claim 1, wherein the processor is further configured to:
send the bio signal to a server for processing.

4. The system recited in claim 1, wherein the processor is further configured to: process the bio signal received from a bio sensor.

5. The system recited in claim 1, wherein the system further comprises:
an ElectroCardioGraphy (ECG) sensor.

6. The system recited in claim 1, wherein the system further comprises:
an ElectroEncephalography (EEG) sensor.

7. The system recited in claim 1, wherein the system further comprises:
an ElectroMyoGraphy (EMG) sensor.

8. The system recited in claim 1, wherein the system further comprises:
an ElectrOculoGraphy (EOG) sensor.

9. The system recited in claim 1, wherein the system further comprises:
an Galvanic Skin Response (GSR) sensor.

10. The system recited in claim 1, wherein the processor is further configured to determine the location using a global positioning system (GPS).

11. The system recited in claim 1, wherein the processor is further configured to display, using a display, an area of the map having the level exceed a threshold differently from an area of the map having the level not exceed the threshold.

12. The system recited in claim 1, wherein the receiving of the collected and aggregated processed bio signals includes communicating with a central archive.

13. The system recited in claim 1, wherein the processor is further configured to use the received bio signal of the user as a ring tone of the mobile device.

14. A method for bio signal based mobile device applications, comprising:
receiving a processed bio signal of a user, the bio signal being an ElectroCardioGraphy (ECG) signal, an ElectroEncephalography (EEG) signal, an ElectroMyoGraphy (EMG) signal, an ElectrOculoGraphy (EOG) signal, an Galvanic Skin Response (GSR) signal, or any combination thereof;
determining whether the user is an authorized user of a mobile device, wherein the determining comprises:
comparing the received bio signal with a stored bio signal of the authorized user of the mobile device; and
in the event that the user is an authorized user of the mobile device, executing a dynamic map application using the processed bio signal, wherein the executing of the dynamic map application comprises:
receiving collected and aggregated processed bio signals of other users;
measuring a level of the processed bio signals of the other users and a level of the received processed bio signal of the user based on a location;
overlaying the level of the measured processed bio signals of the other users and the level of the measured processed bio signal of the user on a map corresponding to the location;
combining the level of the measured processed bio signals in concert with the location with data acquired via another sensor relating to the location, the data including picture, video, audio data, or any combination thereof; and
displaying the level of the processed bio signals of the other users with the level of the received processed bio signal of the user on the map.

15. A computer program product for bio signal based mobile device applications, the computer program product being embodied in a tangible, non-transitory computer readable storage medium and comprising computer instructions for:
receiving a processed bio signal of a user, the bio signal being an ElectroCardioGraphy (ECG) signal, an ElectroEncephalography (EEG) signal, an ElectroMyoGraphy (EMG) signal, an ElectrOculoGraphy (EOG) signal, an Galvanic Skin Response (GSR) signal, or any combination thereof;
determining whether the user is an authorized user of a mobile device, wherein the determining comprises:
comparing the received bio signal with a stored bio signal of the authorized user of the mobile device; and
in the event that the user is an authorized user of the mobile device, executing a dynamic map application using the processed bio signal, wherein the executing of the dynamic map application comprises:
receiving collected and aggregated processed bio signals of other users;

measuring a level of the processed bio signals of the other users and a level of the received processed bio signal of the user based on a location;

overlaying the level of the measured processed bio signals of the other users and the level of the measured processed bio signal of the user on a map corresponding to the location;

combining the level of the measured processed bio signals in concert with the location with data acquired via another sensor relating to the location, the data including picture, video, audio data, or any combination thereof; and displaying the level of the processed bio signals of the other users with the level of the received processed bio signal of the user on the map.

* * * * *